United States Patent [19]

Richter et al.

[11] 3,998,808
[45] Dec. 21, 1976

[54] COMPOSITIONS OF MATTER D-HETERO-1,1-(α-THIOCYANOACETYL) COMPOUNDS

[75] Inventors: Sidney B. Richter, Chicago; Alfred A. Levin, Skokie, both of Ill.

[73] Assignee: Velsicol Chemical Corporation, Chicago, Ill.

[22] Filed: May 18, 1971

[21] Appl. No.: 144,684

Related U.S. Application Data

[63] Continuation-in-part of Ser. No. 731,337, May 22, 1968, abandoned.

[52] U.S. Cl. .................. 260/239 B; 260/239 A; 260/239 E; 260/294.8 R; 260/326.5 S; 260/561 S; 260/454; 260/293.85; 424/302
[51] Int. Cl.² ............ C07D 207/02; C07D 211/16; C07D 223/02
[58] Field of Search .................. 260/326.5 S, 561 S, 260/293.4, 294.8, 239 A, 239 E, 239 B, 454; 424/302

[56] References Cited

UNITED STATES PATENTS

3,102,068  8/1963  Tolbert .................. 260/326.5 E

FOREIGN PATENTS OR APPLICATIONS

481,733  3/1938  United Kingdom .............. 424/302
791,291  2/1958  United Kingdom .............. 424/302

OTHER PUBLICATIONS

Galashina et al., Chem. Abstracts, vol. 54, Cols. 10217–10218, (1960).

*Primary Examiner*—Donald G. Daus
*Assistant Examiner*—David E. Wheeler
*Attorney, Agent, or Firm*—Robert J. Schwarz; Dietmar H. Olesch

[57] ABSTRACT

This invention discloses new chemical compositions of matter having the formula:

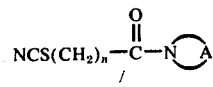

wherein A is a saturated or mono unsaturated aliphatic hydrocarbon chain having from 3 to 7 carbon atoms which optionally contains a maximum of three substituents selected from the group consisting of alkyl, alkoxy and halogen; and n is an integer from 1 to 3. This invention further discloses an insecticidal and fungicidal composition which comprises an inert carrier and, as an essential active ingredient, in a quantity toxic to insects and fungi, a compound of the above description; and a method for the control of insects and fungi which comprises applying to the locus of said insects or fungi an insecticidal and fungicidal composition heretofore described.

9 Claims, No Drawings

COMPOSITIONS OF MATTER D-HETERO-1,1-(α-THIOCYANOACETYL) COMPOUNDS

This application is a continuation-in-part of our co-pending application Ser. No. 731,337 filed May 22, 1968 now abandoned.

This invention relates to new chemical compositions of matter, and more particularly relates to new compounds of the formula:

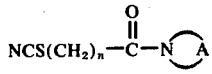

wherein A is a saturated or mono unsaturated aliphatic hydrocarbon chain having from 3 to 7 carbon atoms which optionally contains a maximum of three substituents selected from the group consisting of alkyl, alkoxy and halogen; and n is an integer from 1 to 3.

In a preferred embodiment of this invention A is a saturated or mono unsaturated aliphatic hydrocarbon chain having from 4 to 7 carbon atoms which optionally contains a maximum of three substituents selected from the group consisting of lower alkyl, lower alkoxy, chlorine and bromine. In accordance with the present invention the term lower means a straight chain or branched alkyl group containing up to six carbon atoms. Unexpectedly, the compounds of the present invention are effective as pesticides and particularly as insecticides and fungicides.

The compounds of this invention can be readily prepared from a compound of the formula:

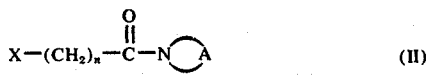 (II)

wherein X is a halogen and A and n are as heretofore described, by reaction with an alkali metal thiocyanate such as sodium thiocyanate or potassium thiocyanate. This reaction is preferably carried out in an inert organic solvent such as ethanol by heating the reactants at the reflux temperature of the mixture for a period of from about 1 to about 8 hours. After the reaction is completed, the desired product can be recovered upon adding a diluent, such as water to the reaction mixture, or by evaporating the solvent from the mixture. The resulting product can be used as such or can be further purified by distillation if the product is an oil, or if a solid, by washing, triturating, recrystallizing, chromatography, extraction or other procedures well known to the art.

Exemplary of the compounds of Formula II suitable for preparing the compounds of this invention are 1-(α-chloroacetyl) aziridine, 1-(α-chloroacetyl)-2-methylaziridine, 1-(α-chloroacetyl)-2-ethylaziridine, 1-(α-chloroacetyl)-2,-2,3-trimethyl-3-propylaziridine, 1-(β-chloropropanoyl) aziridine, 1-(α-chlorobutoyl) aziridine, 1-(α-chloroacetyl) azetidine, 1-(α-chloroacetyl)-2-methylazetidine, 1-(α-chloroacetyl)-3-ethylazetidine, 1-(α-chloroacetyl)-3,3-dimethylazetidine, 1-(α-chloroacetyl)-3,3-dipropylazetidine, 1-(β-chloropropanoyl) azetidine, 1-(α-chloroacetyl) pyrrolidine, 1-(α-chloroacetyl)-2-methylpyrrolidine, 1-(α-chloroacetyl)-3-methylpyrrolidine, 1-(α-chloroacetyl)-2,2-dimethylpyrrolidine, 1-(α-chloroacetyl)-3,4-dimethylpyrrolidine, 1-(α-chloroacetyl)-2,5-dimethylpyrrolidine, 1-(α-chloroacetyl)-2,5-diethylpyrrolidine, 1-(α-chloroacetyl)-2-ethyl-2,5,5-trimethylpyrrolidine, 1-(α-chloroacetyl)-2,2,3,3,5,5-hexamethylpyrrolidine, 1-(β-chloropropanoyl) pyrrolidine, 1-(γ-chlorobutanoyl) pyrrolidine, 1-(α-chloroacetyl) piperidine, 1-(α-chloroacetyl)-2-pipecoline, 1-(α-chloroacetyl)-3-pipecoline, 1-(α-chloroacetyl)-4-pipecoline, 1-(α-chloroacetyl)-2,6-dimethylpiperidine, 1-(α-chloroacetyl)-2-ethylpiperidine, 1-(α-chloroacetyl)-2,4-dimethylpiperidine, 1-(α-chloroacetyl)-2,4,6-trimethylpiperidine, 1-(α-chloroacetyl)-3-isopropylpiperidine, 1-(α-chloroacetyl)-3-n-butylpiperidine, 1-(β-chloropropanoyl) piperidine, 1-(γ-chlorobutanoyl) piperidine, 1-(β-chloropropanoyl)-3-methylpiperidine, 1-(α-chloroacetyl) hexamethylenimine, 1-(α-chloroacetyl)-2-methylhexamethylenimine, 1-(α-chloroacetyl)-4-methylhexamethylenimine, 1-(α-chloroacetyl)-3,4-dimethylhexamethylenimine, 1-(α-chloroacetyl) heptamethylenimine and the like.

When not readily available the starting material compounds of Formula II can be conveniently prepared from a corresponding heterocyclic compound of the formula:

 (III)

wherein A is as hereinabove described, by reaction with a haloalkylene acid of the formula:

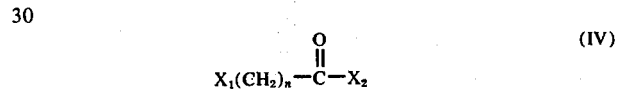 (IV)

wherein $X_1$ and $X_2$ are halogen, preferably chlorine or bromine, and n is an integer from 1 to 3. This reaction can be effected by adding the acid halide of Formula IV to a solution of the heterocyclic compound of Formula III in the presence of an acid scavenger such as tertiary amine. The reaction is preferably carried out in an inert organic solvent, such as benzene, by slowly adding the acid halide to the cyclic amine with vigorous stirring. In most instances the reaction is exothermic and cooling of the reaction mixture can be required. After the completion of the reaction, the product can be recovered by first filtering the reaction mixture to remove any tertiary amine hydrochloride which has formed and thereafter evaporating the solvent to yield the desired product. This product can be used as such or can be further purified by distillation if the product is an oil, or by washing, trituration, recrystallization or other methods common to the art.

Exemplary of suitable heterocyclic compounds of Formula III for preparing the novel compounds of this invention are aziridine, 2-methylaziridine, 2-ethylaziridine, 2-isopropylaziridine, 2,2,3-trimethyl-3-propylaziridine, azetidine, 2-methylazetidine, 3-ethylazetidine, 3,3-dibutylazetidine, pyrrolinde, 2-methylpyrrolidine, 3-methylpyrrolidine, 2,5-dimethylpyrrolidine, 2,2,4-trimethylpyrrolidine, 2-ethyl-2,5,5-trimethylpyrrolidine, piperidine, 4-chloropiperidine, 4-methylpiperidine, 2,6-diethylpiperidine, 4-isopropylpiperidine, 2,3,4-trimethylpiperidine, 3-n-butylpiperidine, hexamethylenimine, 2-methylhexamethylenimine, 3-ethylhexamethylenimine, 3,6-dimethylhexamethylenimine, heptamethylenimine, 4-methylheptamethylenimine, 1,2-dihydropyridine, 1,2,5,6-tetrahydropyridine, pyrrole, 2-pyrroline, 3-pyrroline, 3,5- dimethylpyrrole, 2-ethoxypyrrole, 2-ethyl-2-pyrroline, 4-bromopiperidine, 2-methoxypiperidine, 2-ethoxypiperidine and the like.

The manner in which typical compounds of the present invention can be prepared readily is illustrated in the following examples.

EXAMPLE 1

Preparation of 1-(α-Thiocyanoacetyl) Pyrrolidine 1-(α-Chloroacetyl pyrrolidine (14.7 grams; 0.1 mol), potassium thiocyanate (18 grams; 0.2 mol) and ethanol (50 ml) were charged into a glass reaction flask equipped with a mechanical stirrer and reflux condenser. The reaction mixture was heated at reflux, with stirring, for a period of about 4 hours. The mixture was then cooled and filtered. The filtrate was stripped of solvent to yield a solid product. The solid was extracted with three 200 ml portions of boiling benzene, and the benzene extracts were combined and evaporated under reduced pressure to yield an oil. The oil was poured into pentane wherein it solidified. The solid was recrystallized from a benzene-pentane mixture to yield 1-(α-thiocyanoacetyl) pyrrolidine having a melting point of 95° to 96° C. and having the following elemental analysis; calculated for $C_7H_{10}N_2OS$.

|  | C | H | N | S |
|---|---|---|---|---|
| Theoretical % | 59.97 | 5.49 | 12.72 | 14.55 |
| Found % | 60.22 | 5.53 | 12.76 | 14.31 |

EXAMPLE 2

Preparation of 1-(α-Chloroacetyl)-2,5-dimethylpyrrolidine

A solution of 2,5-dimethylpyrrolidine (15 grams; 0.15 mol) and triethylamine (15 grams) in benzene (150 ml) was charged into a 250 ml glass reaction flask equipped with stirrer, reflux condenser and addition funnel. Chloroacetyl chloride (18 grams; 0.15 mol) was then slowly added, with vigorous stirring, over a period of several minutes. After the addition was completed stirring was continued for about 15 minutes. After this time the reaction mixture was filtered to remove the triethylamine hydrochloride which had formed. The filtered reaction mixture was then stripped of benzene under reduced pressure to yield a dark colored oil. The oil was distilled under vacuum to yield 1-(α-chloroacetyl)-2,5-dimethylpyrrolidine as a colorless oil having a boiling point of 89° to 90° C. at 0.1 mm of mercury pressure, and a refractive index at 25° C. of 1.4863.

EXAMPLE 3

Preparation of 1-(α-Thiocyanoacetyl)-2,5-dimethylpyrrolidine 1-(α-Chloroacetyl)-2,5-dimethylpyrrolidine (10 grams; 0.057 mol), potassium thiocyanate (10.1 grams), sodium iodide (a few crystals) and ethanol (100 ml) were charged into a glass reaction flask equipped with mechanical stirrer and reflux condenser. The reaction mixture was heated at reflux, with stirring, for a period of about 2 hours. After this time the reaction mixture was cooled and filtered. The filtrate was stripped of ethanol under reduced pressure resulting in a solid product. The solid was extracted with two 125 ml portions of hot benzene. The benzene extracts were combined and were evaporated to yield 1-(α-thiocyanoacetyl)-2,5-dimethylpyrrolidine as a light brown oil having a refractive index at 25° C. of 1.5185 and having the following elemental analysis as calculated for $C_9H_{14}N_2OS$.

|  | S |
|---|---|
| Theoretical % | 16.17 |
| Found % | 16.36 |

EXAMPLE 4

Preparation of 1-(β-Chloropropionyl) Pyrrolidine

A solution of pyrrolidine (35 grams; 0.5 mol) and triethylamine (50 grams; 0.5 mol) in benzene (500 ml) is placed in a glass reaction flask equipped with a mechanical stirrer and reflux condenser. β-Chloropropionyl chloride (64 grams; 0.5 mol) is then slowly added with stirring over a period of about 15 minutes. Stirring is continued for a period of about 30 minutes. After this time the reaction mixture is first filtered to remove triethylamine hydrochloride nd is the stripped of benzene to yield 1-(β-chloropropionyl) pyrrolidine.

EXAMPLE 5

Preparation of 1-β-Thiocyanopropionyl) Pyrrolidine 1-(β-Chloropropionyl) pyrrolidine (16 grams; 0.1 mol), potassium thiocyanate (18 grams; 0.2 mol) and ethanol (100 ml) are charged into a glass reaction flask equipped with a mechanical stirrer and reflux condenser. The reaction mixture is then heated at reflux for a period of about 6 hours. After this time the reaction mixture is cooled and filtered. The filtrate is stripped of solvent and the residue is extracted with benzene. The benzene extract is evaporated under reduced pressure to yield 1-(β-thiocyanopropionyl) pyrrolidine as a residue.

EXAMPLE 6

Preparation of 1-(α-Thiocyanoacetyl) Piperidine 1-(γ-Chloroacetyl) piperidine (16 grams; 0.1 mol), potassium thiocyanate (18 grams; 0.2 mol) and ethanol (100 ml) were charged into a glass reaction flask equipped with stirrer and reflux condenser. The reaction mixture was heated at reflux for a period of about 6 hours. After this time the mixture was cooled and filtered. The filtrate was evaporated under reduced pressure to yield a solid product. The solid was then boiled in 400 ml of benzene and the benzene solution filtered. The benzene was evaporated from the filtrate under reduced pressure to yield an oil which gradually solidified upon standing. The solid was triturated with pentane and filtered to yield a tan solid product. The solid product was recrystallized from a chloroform-pentane mixture and was dried to yield 1-(α-thiocyanoacetyl) piperidine having a melting point of 78° to 79° C. and having the following elemental analysis as calculated for $C_8H_{12}N_2OS$.

|  | C | H | N | S |
|---|---|---|---|---|
| Theoretical % | 52.14 | 6.57 | 15.21 | 17.40 |

-continued

|         | C     | H    | N     | S     |
|---------|-------|------|-------|-------|
| Found % | 52.31 | 7.00 | 15.12 | 17.14 |

EXAMPLE 7

Preparation of 1-($\alpha$-Thiocyanoacetyl)-3-pipecoline 1-($\alpha$-Chloroacetyl)-3-pipecoline (17.6 grams; 0.1 mol), potassium thiocyanate (18 grams; 0.2 mol) and ethanol (100 ml) were charged into a glass reaction flask equipped with stirrer and reflux condenser. The reaction mixture was heated at reflux for a period of about 6 hours. After this time the reaction mixture was cooled and filtered. The filtrate was stripped of solvent to yield a solid. The solid was placed in benzene and was boiled for about 30 minutes. The benzene solution was then filtered and stripped of benzene to yield a dark oil. The oil was triturated with pentane to yield a cream colored solid. The solid was then washed with pentane, filtered and dried to yield 15.6 grams of product. The product was recrystallized from a chloroform-pentane mixture to yield 1-($\alpha$-thiocyanoacetyl)-3-pipecoline having a melting point of 70.5 to 72° C. and having the following elemental analysis as calculated for $C_9H_{14}N_2OS$.

|               | C     | H    | N     | S     |
|---------------|-------|------|-------|-------|
| Theoretical % | 54.51 | 7.12 | 14.13 | 16.17 |
| Found %       | 54.72 | 7.35 | 13.93 | 16.11 |

EXAMPLE 8

Preparation of 1-($\alpha$-Thiocyanoacetyl)-4-pipecoline 1-($\alpha$-Chloroacetyl)-4-pipecoline (17.6 grams; 0.1 mol), potassium thiocyanate (18 grams; 0.2 mol) and ethanol (100 ml) were charged into a glass reaction vessel equipped with a mechanical stirrer and reflux condenser. The reaction mixture was then heated at reflux, with stirring, for a period of about 7 hours. After this time the reaction mixture was cooled and filtered. The filtrate was stripped of solvent to yield a solid product. The solid product was then extracted with benzene and the benzene extract was evaporated to yield a dark oil. The oil was triturated with pentane resulting in a tan solid. The solid was recrystallized from a chloroform-pentane mixture to yield 1-($\alpha$-thiocyanoacetyl)-4-pipecoline having a melting point of 72.5° to 74.0° C. and having the following elemental analysis as calculated for $C_9H_{14}N_2OS$.

|               | C     | H    | N     | S     |
|---------------|-------|------|-------|-------|
| Theoretical % | 54.51 | 7.12 | 14.13 | 16.17 |
| Found %       | 54.38 | 7.45 | 14.10 | 16.02 |

EXAMPLE 9

Preparation of 1-($\alpha$-Thiocyanoacetyl)-2,6-dimethylpiperidine 1-($\alpha$-Chloroacetyl)-2,6-dimethylpiperidine (18.9 grams; 0.1 mol), potassium thiocyanate (18 grams; 0.2 mol) and ethanol (100 ml) were charged into a glass reaction flask equipped with a mechanical stirrer and reflux condenser. The reaction mixture was heated at reflux, with stirring, for a period of about 3 hours. After this time the reaction mixture was cooled and filtered. The ethanol was evaporated under reduced pressure to yield a dark solid. The solid was extracted with two 200 ml portions of hot benzene. The benzene extracts were combined, were filtered and treated with activated charcoal. The benzene solution was then evaporated under reduced pressure to yield a dark colored oil which solidified upon standing. The solidified product then crystallized, to yield 1-($\alpha$-thiocyanoacetyl)-2,6-dimethylpiperidine as a pale yellow solid having a melting point of 81° to 82° C. and leaving the following elemental analysis as calculated for $C_{10}H_{16}N_2OS$.

|               | C     | H    | N     | S     |
|---------------|-------|------|-------|-------|
| Theoretical % | 56.57 | 7.60 | 13.20 | 15.10 |
| Found %       | 56.70 | 8.02 | 13.24 | 14.92 |

EXAMPLE 10

Preparation of 1-($\alpha$-Thiocyanoacety)-2,4,6-trimethylpiperidine 1-($\alpha$-Chloroacetyl)-2,4,6-trimethylpiperidine (18 grams; 0.9 mol), potassium thiocyanate (18 grams; 0.2 mol), sodium iodide (a few crystals) and ethanol (100 ml) were charged into a glass reaction flask equipped with a mechanical stirrer and reflux condenser. The reaction mixture was heated at reflux for a period of about 3 hours. After this time the mixture was cooled and filtered. The filtrate was evaporated leaving a solid product. The solid was then extracted with two 150 ml portions of hot benzene. The extracts were combined and evaporated under reduced pressure to yield an oil. This oil was refined by chromatography using Fuller's earth as an adsorbent and benzene as the elluent. The first 1000 ml of eluent were collected from the column and were stripped of benzene to yield 1-($\alpha$-thiocyanoacetyl)-2,4,6-trimethylpiperidine as a yellow oil having a refractive index of 1.5183 at 25° C. and having the following elemental analysis as calculated for $C_{11}H_{18}N_2OS$.

|               | S     | N     |
|---------------|-------|-------|
| Theoretical % | 13.23 | 11.56 |
| Found %       | 14.04 | 12.04 |

EXAMPLE 11

Preparation of 1-($\alpha$-Chloro-n-butanoyl)-2-pipecoline

A solution of 2-pipecoline (49 grams; 0.5 mol) and triethylamine (50 grams; 0.5 mol) in benzene (100 ml) is placed in a 2 liter glass reaction flask equipped with stirrer and reflux condenser. $\gamma$-Chloro-n-butanoyl chloride (70 grams; 0.5 mol) is slowly added with stirring over a period of about 15 minutes. Stirring of the reaction mixture is continued for an additional period of about 1 hour. After this time the mixture is filtered and stripped of benzene to yield 1-($\gamma$-chloro-n-butanoyl)-2-pipecoline.

EXAMPLE 12

Preparation of 1-(α-Thiocyano-n-butanoyl)-2-pipecoline 1-(α-Chloro-n-butanoyl)-2-pipecoline (20 grams; 0.1 mol), potassium thiocyanate (18 grams; 0.2 mol) and ethanol (100 ml) are charged into a glass reaction flask equipped with stirrer and reflux condenser. The reaction mixture is heated at reflux, with stirring, for a period of about 4 hours. After this time the reaction mixture is cooled and filtered. The filtrate is evaporated under reduced pressure and the residue extracted with hot benzene. The benzene extract is then evaporated to yield 1-(α-thiocyano-n-butanoyl)-2-methyl-pipecoline.

EXAMPLE 13

Preparation of 1-(α-Chloroacetyl) Hexamethylenimine

A solution of hexamethylenimine (50 grams; 0.5 mol) and triethylamine (50 grams; 0.5 mol) in benzene (1000 ml) was placed in a 2 liter glass reaction flask equipped with stirrer and reflux condenser. Chloroacetyl chloride (56.5 grams; 0.5 mol) was slowly added, with stirring, over a period of about 15 minutes. An exotherm was observed. Stirring was continued for an additional period of 15 minutes, after which time the reaction mixture was cooled and filtered. The filtered solution was stripped of benzene resulting in a dark colored oil. The oil was then distilled to yield 1-(α-chloroacetyl) hexamethylenimine as a pale yellow oil having a boiling point of 108° to 110° C. and 0.9 mm of mercury pressure and having a refraction index of 1.5078 at 25° C.

EXAMPLE 14

Preparation of 1-(α-Thiocyanoacetyl) Hexamethylenimine

N-(α-Chloroacetyl) hexamethylenimine (16.8 grams; 0.1 mol), potassium thiocyanate (18 grams; 0.2 mol), sodium iodide (a few crystals) and ethanol (100 ml) were charged into a glass reaction vessel equipped with stirrer and reflux condenser. The reaction mixture was heated at reflux for a period of about 2 hours. After this time the reaction mixture was cooled and filtered. The filtrate was poured into 1500 ml of water resulting in the formation of a white precipitate. The precipitate was recovered by filtration and was dissolved in ether. The ethereal solution was then dried over anhydrous magnesium sulfate. The drying agent was filtered and the ethereal solution was concentrated to about 20% of its original volume and was poured into pentane forming a white solid. The solid was recovered by filtration, was dried and was recrystallized from a pentane-ether mixture to yield 1-(α-thiocyanoacetyl) hexamethylenimine having a melting point of 84° to 85.5° C. and having the following elemental analysis as calculated for $C_9H_{14}N_2OS$.

|  | C | H | S | N |
|---|---|---|---|---|
| Theoretical % | 54.51 | 7.12 | 16.17 | 14.13 |
| Found % | 54.53 | 7.19 | 16.17 | 14.12 |

EXAMPLE 15

Preparation of 1-(α-Chloroacetyl)-1,2,5,6-Tetrahydropyridine

A solution of 1,2,5,6-tetrahydropyridine (41.5 grams; 0.5 mol) and triethylamine (50 grams; 0.5 mol) in benzene (1 l.) was placed into a 2 l. glass reaction flask equipped with a mechanical stirrer, reflux condenser and addition funnel. Chloroacetyl chloride (56.5 grams; 0.5 mol) was slowly added, with stirring, over a period of about 15 minutes. After the addition was completed stirring was continued for an additional period of about 15 minutes. After this time the reaction mixture was cooled and filtered to remove the triethylamine hydrochloride which had formed. The remaining benzene solution was stripped of solvent to yield a dark colored oil. The oil was then distilled under reduced pressure, to yield 1-(α-chloroacetyl)-1,2,5,6-tetrahydropyridine as a pale yellow oil having a boiling point of 88° to 91° C. at 0.35 mm Hg. pressure, an index of refraction of 1.5224 at 25° C. and having the following elemental analysis as calculated for $C_7H_{10}ClNO$.

|  | Cl |
|---|---|
| Theoretical % | 22.72 |
| Found % | 23.20 |

EXAMPLE 16

Preparation of 1-(α-Thiocyanoacetyl)-1,2,5,6-tetrahydropyridine 1-(α-Chloroacetyl)-1,2,5,6-tetrahydropyridine (16 grams; 0.1 mol), potassium thiocyanate (18 grams; 0.2 mol), sodium iodide (several crystals), and ethanol (100 ml) were charged into a glass reaction flask equipped with stirrer and reflux condenser. The reaction mixture was heated at reflux, with stirring, for a period of about 2 hours. After this time the reaction mixture was cooled, filtered and poured into a large volume of cold water resulting in the formation of a solid. The solid was recovered by filtration and was dissolved in ether. The aqueous filtrate was extracted with ether and the extract combined with the ethereal solution. The combined solutions were dried over anhydrous magnesium sulfate and filtered. The dried solutions were then stripped of ether and the resulting yellow solid recrystallized from ether to yield 1-(γ-thiocyanoacetyl)-1,2,5,6-tetrahydropyridine having a melting point of 72.5° to 74° C. and having the following elemental analysis as calculated for $C_8H_{10}N_2OS$.

|  | C | H | N | S |
|---|---|---|---|---|
| Theoretical % | 52.72 | 5.58 | 15.38 | 17.59 |
| Found % | 52.73 | 5.58 | 14.93 | 17.34 |

EXAMPLE 17

Preparation of 1-(α-Chloroacetyl) Azetidine

A solution of azetidine (28 grams; 0.5 mol) and triethylamine (50 grams; 0.5 mol) in benzene (500 ml) is placed in a glass reaction flask equipped with stirrer and reflux condenser and addition funnel. Chloroacetyl chloride (56.5 grams; 0.5 mol) is then slowly added, with stirring, over a period of about 30 minutes. Stirring is continued for an additional period of about 30 minutes. After this time, the reaction mixture is first filtered to remove triethylamine hydrochloride and then stripped of benzene to yield an oil. This oil is then distilled under partial pressure to yield 1-(α-chloroacetyl) azetidine.

EXAMPLE 18

Preparation of 1-(α-Thiocyanoacetyl) Azetidine 1-(α-Chloroacetyl) azetidine (13 grams; 0.1 mol), potassium thiocyanate (18 grams; 0.18 mol) and ethanol (100 ml) are charged into a glass reaction flask equipped with stirrer and reflux condenser. The reaction mixture is then heated at reflux, with stirring, for a period of about 4 hours. After this time the reaction mixture is cooled and filtered. The filtrate is then stripped of ethanol leaving a residue. The residue is extracted twice with hot benzene and the two benzene extracts are combined. The benzene extract is then evaporated under reduced pressure to yield 1-(α-thiocyanoacetyl) azetidine as a residue.

Other compounds within the scope of this invention can be prepared by the procedures described in the foregoing examples. Presented in the following examples are the essential ingredients required to prepare the indicated named compounds according to the procedures heretofore described.

EXAMPLE 19

2-Ethylazetidine + α-chloroacetyl chloride + potassium thiocyanate = 1-(α-thiocyanoacetyl)-2-ethylazetidine.

EXAMPLE 20

3,3-Di-n-propylazetidine + α-chloroacetyl chloride + potassium thiocyanate = 1-(α-thiocyanoacetyl)-3,3-di-n-propylazetidine.

EXAMPLE 21

2,4-Dimethylazetidine + β-chloropropionyl chloride + potassium thiocyanate = 1-(β-thiocyanate = 1-(β-thiocyanopropionyl)-2,4-dimethylazetidine.

EXAMPLE 22

3-Isopropylpyrrolidine + γ-chloro-n-butanoyl chloride + potassium thiocyanate = 1-(γ-thiocyano-n-butanoyl)-3-isopropylpyrrolidine.

EXAMPLE 23

2,2,4-Trimethylpyrrolidine + α-chloroacetyl chloride + potassium thiocyanate = 1-(γ-chloroacetyl)-2,2,4-trimethylpyrrolidine.

EXAMPLE 24

Pyrrolidine + γ-chloro-n-butanoyl chloride 30 potassium thiocyanate = 1-(γ-thiocyano-n-butanoyl) pyrrolidine.

EXAMPLE 25

Piperidine + β-chloropropionyl chloride + potassium thiocyanate = 1-(β-thiocyanopropionyl) piperidine.

EXAMPLE 26

Hexamethylenimine + β-chloropropionyl chloride + potassium thiocyanate = 1-(β-thiocyanopropionyl) hexamethylenimine.

EXAMPLE 27

Hexamethylenimine + γ-chloro-n-butanoyl chloride + potassium thiocyanate = 1-(γ-thiocyano-n-butanoyl) hexamethylenimine.

EXAMPLE 28

3,6-Dimethylhexamethylenimine + γ-chloroacetyl chloride + potassium thiocyanate = 1-(α-thiocyanoacetyl)-3,6-dimethylhexamethylenimine.

EXAMPLE 29

Heptamethylenimine + α-chloroacetyl chloride + potassium thiocyanate = 1-(α-thiocyanaoacetyl) heptamethylenimine.

EXAMPLE 30

4-Bromopiperidine + α-chloroacetyl chloride + potassium thiocyanate = 1-(α-thiocyanoacetyl)-4-bromopiperidine.

EXAMPLE 31

2-Methoxypiperidine + α-chloroacetyl chloride + potassium thiocyanate = 1-(α-thiocyanoacetyl)-2-methoxypiperidine.

EXAMPLE 32

2-Pyrroline + α-chloroacetyl chloride + potassium thiocyanate = 1-(α-thiocyanoacetyl)-2-pyrroline.

For practical use as pesticides, the compounds of this invention are generally incorporated into pesticidal compositions which comprise an inert carrier and a pesticidally toxic amount of such a compound. Such pesticidal compositions, which can also be called formulations, enable the active compound to be applied conveniently to the site of the pest infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculities, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of pesticides can be dispersed under superatmospheric pressure as aerosols. However, preferred liquid pesticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the pest infestation. The emulsifiers most commonly used in these concentrates are nonionic or mixtures of nonionic with anionic surface-active agents.

A typical pesticidal composition according to this invention is illustrated by the following example, in which the quantities are in parts by weight.

EXAMPLE 33

| Preparation of a Dust | |
|---|---|
| Product of Example 3 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the pest infestation.

When used as an insecticide the compounds of this invention can be applied in any manner recognized by the art. One method for destroying insects comprises applying to the locus of the insect infestation, an insecticidal composition comprising an inert carrier and as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists, and the like.

The compounds of the present invention are also useful when combined with other insecticides in the insecticidal compositions heretofore described. These other insecticides can comprise from about 5% to about 95% of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol, and the like; organic phosphorous compounds such as TEPP, schradan, ethion, parathion, methyl parathion, EPN, demeton, carbonphenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP, and the like; organic nitrogen compounds such as dinitro-o-cresol, dinitrocyclohexylphenol, DNB, DNP, binapacril, azobenzene, and the like; organic carbamate compounds such as carbaryl, ortho 5353, and the like; organic sulfur compounds such as phenothiazine, phenoxathin, lauryl thiocyanate, bis(2-thiocyanoethyl) ether, isobornyl thiocyanoacetate, and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects such as the Mexican bean beetle, the southern armyworm; the piercing-sucking insects, such as the pea aphid, the cereal leaf beetle, the house fly, the grape leafhopper, the chinch bug, the lygus bugs, oyster shell scale, the California red scale, the FLorida red scale, the soft scale and mosquitoes; the internal feeders, including bores such as the European corn borer, the peach twig borer and the corn earworm, worms or weevils such as the codling moth, alfalfa weevil, cotton boll weevil, pink bollworm, plum curculio, red banded leaf roller, melonworm, cabbage looper and apple maggot, leaf miners such as the apple leaf miner, birch leaf miner and beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation, and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The new compounds of this invention are not only effective for the control of insect pests but also exhibit fungicidal activity, that is, they kill, inhibit, or inactivate a fungus so that it does not grow. Practically, these compounds can be used to prevent fungi and molds from harming cloth, wood, plants, seeds, fruit, animals, or whatever else they attack. The fungicidal compounds should preferably be applied before the infection has occurred and certainly before it has progressed very far.

The fungicides of this invention can be applied in any manner recognized by the art. The concentration of the new compounds of this invention in fungicidal compositions will vary greatly with the type of formulation and the purpose for which it is designed but generally the fungicidal compositions will comprise from about 0.05 to about 95 percent by weight of the active compounds of this invention. In a preferred embodiment of this invention, the fungicidal compositions will comprise from about 5 to about 75 percent by weight of the active compound. The compositions can also comprise such additional substances as other pesticides, spreaders, adhesives, stickers, fertilizers, activators, synergists, and the like.

The compounds of the present invention are also useful when combined with other fungicides in the fungicidal compositions heretofore described. The other fungicides can comprise from about 5 percent to about 95 percent of the active ingredients in the fungicidal compositions. Use of combinations of these other fungicides with the compounds of the present invention provides fungicidal compositions which are more effective in controlling fungi and often provide results unattainable with separate compositions of the individual fungicides. The other fungicides, with which the compounds of this invention can be used in the fungicidal compositions to control fungi, can include fungicides such as 2-amino-butane, bordeaux mixture, ammonium dimethyl dithiocarbamate, benzoyl trimethyl ammonium bromide, cadmium sulfate, captan, chloranil, copper sulfate, cycloheximide, dichlone, 2,4-dichloro-6-(2-chloroanilino)-s-triazine, DDT, dichloran, p-dimethylaminobenzenediazo sodium sulfonate, dinocap, diphenylmercuri 8-hydroxyquinolinate, dodine, ethylmercuric chloride, ferbam, folpet, gliodin, maneb, metham, mezineb, nabam, pentachloronitrobenzene, PMA, phenylmercuric urea, streptomicin, thiram, zineb, ziram, difolatan, PCNB, and the like.

Such fungicides can also be used in the methods and compositions of this invention in the form of their esters, amides, and other derivatives whenever applicable to the particular parent compound.

When the compounds of this invention are used as agricultural fungicides, they can be applied to plant foliage, to seeds, to the soil, or to such parts of plants as the fruits themselves. Plants are susceptible to a great many diseases which cause widespread damage; and among some of the more important which can be mentioned are late blight on tomato, powdery mildew on cucumber (*Erisiphe cichoracearum*), cereal leaf rust on wheat (*Puccinia rubigo-vera*), and such common soil fungi as fusarium wilt (*Fusarium oxysporum*), the seed rot fungus (*Phythium debaranum*), and the sheath and culm blight (*Rhizoctonia solani*). The new compounds of this invention can also be employed as industrial fungicides to control a variety of fungi which attack such materials as adhesives, cork, paints, lacquers, leather, wood, plastics, and textiles such as cotton and wool.

The quantity of active compound of this invention to be used for good disease control will depend on a variety of factors, such as the particular disease involved, the intensity of the infestation, formulation, weather, type of crop and the like. Thus, while the application of only one or two ounces of active compound per acre of a crop may be sufficient to control a light infestation of certain fungi, a pound or more of active compound per acre may be required to control a heavy infestation of a hardy species of fungus.

The insecticidal utility of the compounds of the present invention was demonstrated in experiments carried out for the control of the housefly (*Musca domestica*).

In one experiment, designated as the housefly knockdown test, 50, 3-day-old, unsexed, adult houseflies were anesthetized with carbon dioxide gas and placed into a fine mesh wire cage. The flies were allowed to recover completely from the effects of the carbon dioxide gas and were then sprayed with a test formulation containing 3500 ppm of the test compound. After 30 minutes the knockdown value of the test compound was determined. Knockdown is considered as an individual fly that is unable to move its body length, and the knowndown value is given as a percent of down flies based on the number of down flies in comparison to a control. The results of this experiment are shown in Table I.

In another experiment designated as the housefly topical test, each of fifty flies was contacted with a test compound by applying 1 ml of test formulation containing 3500 ppm of active chemical to the dorsum of its thorax. The flies were then placed in a wire mesh cage where they were supplied with sugar syrup. At the end of a 24 hour period the mortality of the flies was observed and rated in comparison to a control. The results of this experiment are also shown in Table I.

TABLE I

| Test Compound | % Control | |
|---|---|---|
| | Housefly Knockdown Test | Housefly Topical Test |
| 1-(γ-Thiocyanoacetyl)-3-pipecoline | 100 | 100 |
| 1-(γ-Thiocyanoacetyl)-4-pipecoline | 100 | 100 |
| 1-(γ-Thiocyanoacetyl)-2,5-dimethylpyrrolidine | 100 | 100 |
| 1-(γ-Thiocyanoacetyl)-2,6-dimethylpiperidine | 92 | 94 |
| 1-(γ-Thiocyanoacetyl) hexamethylenimine | 94 | 31 |

The insecticidal activity of the compounds of this invention was further illustrated in an experiment for the control of the pea aphid (*Acyrthosiphon pisum*). In this experiment a ten day old Laxton pea plant contained in a small plastic pot was infested with ten adult pea aphids. The plant and pea aphids were then sprayed with the test compound formulated as an aqueous emulsion of an acetone solution, at a concentration of 3500 ppm. The infested plants were then placed in a holding chamber maintained at a constant temperature for a period of 48 hours. After this time the mortality of the aphids was determined and rated on a percent basis in comparison to a control. In this experiment the compounds 1-(α-thiocyanoacetyl) pyrrolidine and 1-(α-thiocyanoacetyl)-2,6-dimethylpiperidine gave 100% mortality of the pea aphids.

The fungicidal activity of the compounds of the present invention was demonstrated in experiments carried out for control of fungi. In one experiment carried out for the protection of wheat against leaf rust of wheat (*Puccinia rubigo-vera*), 6 day old wheat plants were sprayed with 1000 ppm solutions of the test compounds. After the spray film had dried, the plants were inoculated by shaking a 9 to 13 day old leaf rust of wheat culture over the foliage. Immediately after inoculation the plants were placed in a 20° C. moist chamber overnight. The plants were then transferred to a greenhouse and kept there for a period of about 8 days. After this time the extent of the disease was observed and rated in comparison with untreated controls. The results are shown in Table II.

TABLE II

| Test Compound | % Control |
| --- | --- |
| 1-(γ-Thiocyanoacetyl)-3-pipecoline | 90 |
| 1-(γ-Thiocyanoacetyl)-4-pipecoline | 99 |
| 1-(γ-Thiocyanoacetyl) pyrrolidine | 98 |
| 1-(γ-Thiocyanoacetyl)-2,6-dimethylpiperidine | 96 |

We claim:

1. A compound of the formula $$NCS(CH_2)_n-\overset{O}{\underset{\|}{C}}-N\underset{}{\overset{}{\bigcirc}}A$$

wherein A is a saturated or mono olefinically unsaturated aliphatic hydrocarbon chain having from 4 to 7 carbon atoms which optionally contains a maximum of three substituents selected from the group consisting of lower alkyl, lower alkoxy and halogen; and $n$ is an integer from 1 to 3.

2. A compound of claim 1 wherein A is a saturated aliphatic hydrocarbon chain having from 4 to 7 carbon atoms which optionally contains from 1 to 3 substituents selected from the group consisting of lower alkyl, lower alkoxy and halogen.

3. A compound of claim 1 of the formula

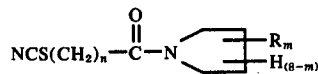

wherein R is selected from the group consisting of lower alkyl, lower alkoxy and halogen; $m$ is an integer from 0 to 3; and $n$ is an integer from 1 to 3.

4. A compound of claim 1 of the formula

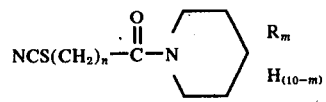

wherein R is selected from the group consisting of lower alkyl, lower alkoxy and halogen; $m$ is an integer from 0 to 3; and $n$ is an integer from 1 to 3.

5. A compound of claim 1 of the formula

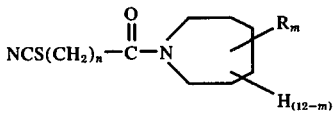

wherein R is selected from the group consisting of lower alkyl, lower alkoxy and halogen; $m$ is an integer from 0 to 3; and $n$ is an integer from 1 to 3.

6. The compound of claim 1, 1-(α-thiocyanoacetyl) pyrrolidine.

7. The compound of claim 1, 1-(α-thiocyanoacetyl)-2,5-dimethylpyrrolidine.

8. The compound of claim 1, 1-(α-thiocyanoacetyl)-2,6-dimethylpiperidine.

9. The compound of claim 1, 1-(α-thiocyanoacetyl) hexamethylenimine.

* * * * *